United States Patent [19]

Naggi et al.

[11] Patent Number: 4,948,881

[45] Date of Patent: Aug. 14, 1990

[54] PROCESS FOR THE DEPOLYMERIZATION AND SULFATION OF POLYSACCHARIDES

[75] Inventors: Annamaria Naggi, Legnano; Giangiacomo Torri, Bergamo, both of Italy

[73] Assignee: Sanofi, Paris, France

[21] Appl. No.: 302,147

[22] Filed: Jan. 27, 1989

Related U.S. Application Data

[63] Continuation of Ser. No. 136,967, Dec. 23, 1987, abandoned, which is a continuation-in-part of Ser. No. 760,353, Jul. 29, 1985, abandoned, which is a continuation-in-part of Ser. No. 677,249, Dec. 3, 1984, abandoned, which is a continuation-in-part of Ser. No. 565,614, Dec. 27, 1983, abandoned.

[51] Int. Cl.$^5$ .................... A61K 31/725; C08B 37/10
[52] U.S. Cl. .................................. 536/20; 536/4.1; 536/21; 536/22; 536/33; 536/56; 536/59; 536/102; 536/109; 536/112; 536/118; 536/122; 536/124; 536/126
[58] Field of Search ...................... 536/4.1, 20, 21, 22, 536/33, 56, 59, 102, 109, 112, 118, 122, 124, 126

[56] References Cited

U.S. PATENT DOCUMENTS

| 2,697,093 | 12/1954 | Jones | 536/111 |
|---|---|---|---|
| 2,755,275 | 7/1956 | Cushing et al. | 536/20 |
| 2,832,766 | 4/1958 | Wolfrom | 536/20 |
| 3,057,855 | 10/1962 | Smith et al. | 536/118 |
| 3,075,965 | 1/1963 | Touey et al. | 536/118 |
| 3,578,657 | 5/1971 | Ricard et al. | 536/112 |
| 3,686,164 | 8/1972 | Unger et al. | 536/118 |
| 3,951,949 | 4/1976 | Hamuro et al. | 536/111 |
| 4,266,077 | 5/1981 | Conrow et al. | 424/101 |
| 4,727,063 | 2/1988 | Naggi et al. | 514/56 |

OTHER PUBLICATIONS

Journal of the American Chemical Society, M. L. Wolfrom et al., 1959, 81, pp. 1764-1766.
Chemical Abstracts, vol. 76, 1972, abstracts, 76:59936g 76:113456r.

Primary Examiner—Ronald W. Griffin
Attorney, Agent, or Firm—Stevens, Davis, Miller & Mosher

[57] ABSTRACT

Process for the depolymerization and sulfation of polysaccharides by reaction of said polysaccharides with a sulfuric acid/chlorosulfonic acid mixture.

15 Claims, 6 Drawing Sheets

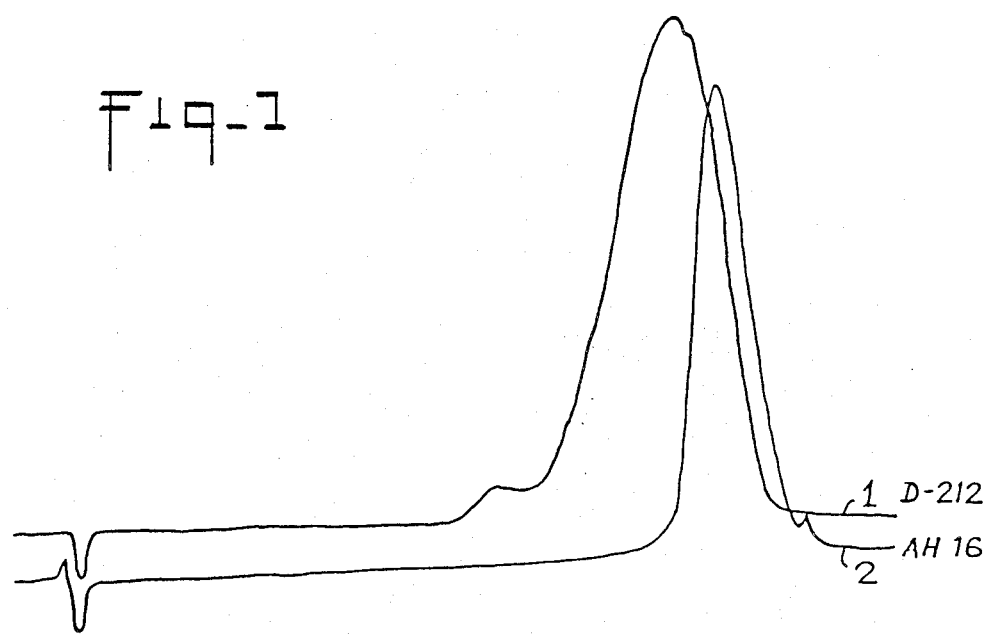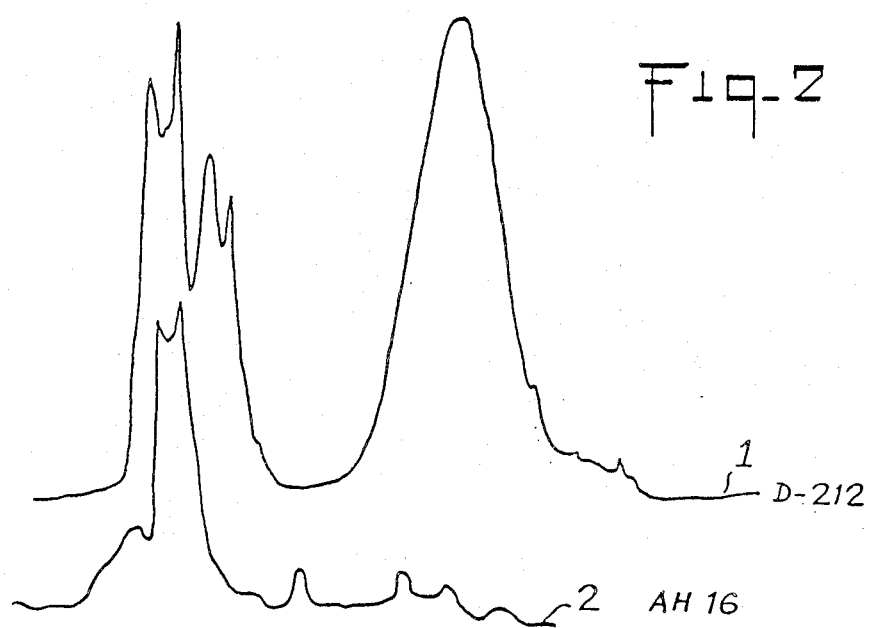

D-2121B

AH 18

D-212

AH-19

D-479
AH-108

D-479
AH-108

D-98
AH-118

D-98
AH-118

PROCESS FOR THE DEPOLYMERIZATION AND SULFATION OF POLYSACCHARIDES

CROSS REFERENCES TO RELATED APPLICATION

This application is a continuation of application Ser. No. 136,967, filed Dec. 23, 1987, which in turn is a continuation-in-part of application Ser. No. 760,353 filed July 29, 1985, which in turn is a continuation-in-part of application Ser. No. 677,249, filed Dec. 3, 1984, which in turn is a continuation-in-part of application Ser. No. 565,614, filed Dec. 27, 1983, all abandoned.

FIELD OF THE INVENTION

The present invention relates to a process for the depolymerisation and sulfation of polysaccharides. It also relates to a chitosane 6-sulfate.

BACKGROUND OF THE INVENTION

Sulfated polysaccharides are compounds having a great importance in cosmetic, textile, alimentary and pharmaceutical industry. More particularly their use is recommended in prevention of venous thrombosis (I. B. Jacques, Pharmacological Reviews, 1979, 31, 99–166).

Besides, low molecular weight sulfated polysaccharides have been proposed as antithrombotic non-anticoagulant agents, thus involving a weak hemorragic risk (D. P. Thomas, Seminars in Hematology, 1978, 15, 1–17).

Chitosan is a polysaccharide consisting of 400 to 6000 beta-D(1,4)-glucosamine subunits containing from zero to 30% of acetyl groups attached to the amino group of glucosamine.

Methods for the sulfation of chitosan are described in the literature.

Such methods afford chitosan sulfates having the sulfate groups randomly fixed to one of the hydroxy groups in the 3 and 6 positions and to the amino groups in the 2 position of the glucosamine unit.

PRIOR ART

Low molecular weight sulfated polysaccharides are obtained by sulfation of low molecular weight polysaccharides. The sulfation is generally carried out by treatment with chlorosulfonic acid in pyridine (M. L. Wolfrom et al., J. Am. Chem. Soc. 1953, 75, 1519) or with adducts of sulfur trioxide (sulfuric anhydride) with aprotic solvents (P. L. Whilster, W. W. Spencer, Methods Carbohydrate Chem., 1964, 4, 297-298; R. L. Whilster, ibid., 1972, 6, 426–429).

The low molecular weight polysaccharides are generally obtained by fractionating a whole of species with various molecular weights or by controlled depolymerisation of non-fractionated polysaccharides with nitrous acid.

However, the known sulfation processes present some disadvantages, particularly due to the operating conditions and to the difficulty of controlling the reaction.

The depolymerisation processes, on the other hand, also present the disadvantage of giving a certain percent of inactive products.

In the case of N-sulfated polysaccharides such as heparin, the depolymerisation processes also involve a hydrolysis of said N-sulfated group, essential to the biological activity of heparin.

French Patent No. 1,093,099 discloses a process for the preparation of chitosan sulfate by reaction of chitosan with a sulfating agent. According to said patent, the sulfating agent may be a mixture of sulfur trioxide and sulfur dioxide or other agents such as chlorosulfonic acid in pyridine or fuming sulfuric acid.

The examples of said patent specifically describe the reaction with a mixture of sulfur trioxide and sulfur dioxide which affords a chitosan sulfate having a sulfur percent of 14.8%, 9%, 16.5%, 14.7% and 17.56% (assuming a completely deacetylated product), corresponding to a substitution degree (group sulfate per glucosamine subunit) of 1.22, 0.75, 1.36, 1.21 and respectively, 1.45.

The patent does not state where the sulfate group is introduced, but it has been subsequently demonstrated that the sulfur trioxide/sulfur dioxide reaction introduces the sulfate group also on the 2-amino group of chitosan.

An example of the same patent specifically describes the reaction of chitosan with chlorosulfonic acid in pyridine. Such a reaction, however, gives a product having a sulfate group on the amine in the 2 position.

Therefore, this process is not selective for the 6position.

U.S. Pat. No. 2,755,275 claims a process for sulfating chitin by reaction of the starting material with chlorosulfonic acid or sulfur trioxide in an halogenated solvent. In the broader disclosure of said patent, chitosan can also been used as a starting material. However, the process claimed induces, in the case of chitosan, a concurrent sulfation of the free amino group in the 2 position.

Nagasawa et al. (Chem. Pharm. Bull. 1972, 20, 157–162—C.A. 76, 113456r) describe the sulfation of chitosan using concentrated sulfuric acid. The authors clearly state that the compound thus obtained is almost totally N-sulfated.

Generally the sulfation of chitosan according to the known methods leads to products completely or partially sulfated on the free amino group at the 2 position and, concurrently, on the hydroxy groups at the 3 and 6 positions.

None of the processes which are described in the literature allows the preparation of a chitosan having the primary hydroxy group of substantially all the glucosamine subunits selectively sulfated and, concurrently, no sulfate group in the 2 and 3 position.

Thus, a chitosan 6-sulfate having no sulfate group both on the 2-amino and 3-hydroxy functions of the glucosamine subunits has not been heretofore described.

SUMMARY OF THE INVENTION

It has now surprisingly been found that by reacting a polysaccharide with a mixture of sulfuric acid and chlorosulfonic acid both a depolymerisation and a sulfation take place concurrently. This finding is particularly surprising, especially because it has also been found that the sulfation is always total on the possibly present primary hydroxy groups.

It has also surprisingly been found that by treating a chitosan with a mixture of sulfuric acid and chlorosulfonic acid a selective sulfation of the hydroxy group at the 6 position is obtained.

It has finally been found that the depolymerization does not involve any further sulfation and that a depolymerized chitosan selectively sulfated in the 6 position is obtained in very high yields.

DETAILED DESCRIPTION

Figure 3:
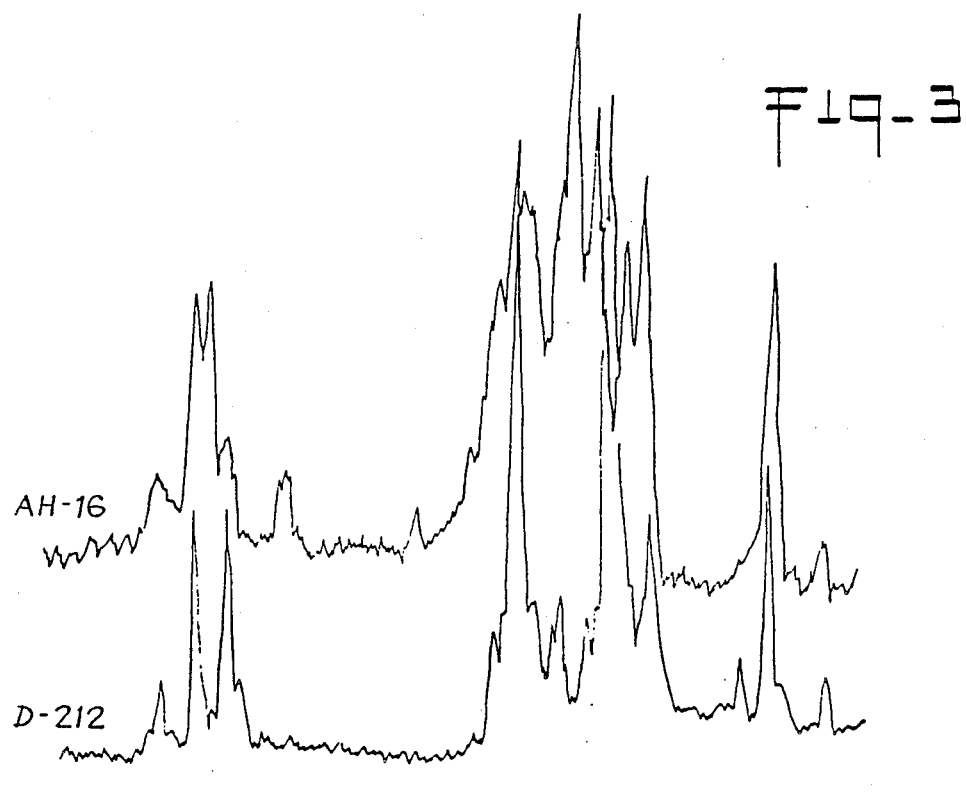

Thus, it is an object of the present invention to provide a process for the depolymerisation and sulfation of polysaccharides which comprises reacting said polysaccharide with a mixture of sulfuric acid and chlorosulfonic acid.

It is also an object of the present invention to provide a chitosan selectively sulfated at the 6 position.

In the mixture, the two acids are concentrated; preferably their concentration is at least 95% by weight.

The ratio of the two acids is highly variable and may go from traces of chlorosulfonic acid in sulfuric acid up to a ratio sulfuric acid:chlorosulfonic acid 4:1 by volume. Advantageously, the ratio sulfuric acid/chlorosulfonic acid varies between 4:1 and 1:1, a ratio of about 2:1 being particularly preferred.

The reaction temperature and the concentration of the starting product in the sulfuric acid/chlorosulfonic acid mixture may vary according to the nature of the substrate. For example, the poor solubility of cellulose suggests more elevated dilutions, whereas, in the case of chitosan, it is possible to use a higher concentration and to carry out the reaction at a relatively low temperature.

Generally, the reaction temperature may vary between $-20°$ and $+40°$ C.; after a period varying from some minutes to 2 hours, according to the reaction temperature, the reaction is complete and the depolymerized and sulfated polysaccharide is isolated according to the conventional techniques, for example by neutralization and dialysis, by chromatography or by lyophilisation.

The depolymerized and sulfated polysaccharide may also be isolated by pouring the reaction mixture in a solvent wherein the end product is insoluble, for example in a non-polar, aprotic solvent such as diethyl ether, by filtering the precipitate which forms and purifying it according to the techniques known in the sugars chemistry.

The depolymerized and sulfated polysaccharides may further be isolated as alkali metal salts thereof according to the usual methods, for example by lyophilisation or by evaporation under reduced pressure, and characterized according to the known physicochemical methods.

Other salts, such as the calcium salt, may be obtained starting from the alkaline salts, preferably from the sodium salt, by exchange reaction with the appropriate salt, for example with a calcium salt, by optionally using an ion exchange resin.

In the case of a starting polysaccharide having a very high polymerization degree, for example in the case of chitosan, chitin or cellulose, it is advantageous to submit said starting product to a previous depolymerisation according to known methods, for example by treatment with nitrous acid. The product thus previously partially depolymerized can be further depolymerized and sulfated according to the process of the present invention.

The starting polysaccharide having a very high molecular weight may also be submitted to the process of the present invention twice. In such a case it is not even necessary to isolate the depolymerized product; a further amount of the sulfuric acid/chlorosulfonic acid mixture can be added to the reaction mixture, for example after the first hour. Surprisingly, this procedure does not involve any degradation or further sulfation. For example, in the case of cellulose a compound depolymerized and totally sulfated in the 6-position, i.e. on the primary hydroxy group, is obtained according to this procedure.

The process of the present invention may be carried out on the known polysaccharides. Suitable starting materials are heparin, heparansulfates, chitosan, chitin, cellulose, starch, guaran, the chondroitinsulfates, sulfates, inulin, dermatansulfate, keratan, the mannans, scleroglucan, the galactomannans, the dextrans, the galactans, xanthan.

The process of the present invention is advantageous for its selectivity and conveniences in handling.

In the case of heparin, for example, there is obtained a depolymerized and "supersulfated" heparin having a molecular weight of from 2000 and 9000 and a sulfation degree higher than that of the starting heparin. In this depolymerized and "supersulfated" heparin, all of the primary hydroxy groups are sulfated.

In the case of chitosan, the reaction with a sulfuric acid/chlorosulfonic acid mixture according to the present invention provides a chitosan with a depolymersation degree which is unknown because the molecular weight, as that of the starting compound, is too high, but which is supposed to be depolymerized. The primary hydroxy groups of this compound is selectively sulfated, without any variation on the secondary hydroxy group or on the free amino group.

In addition, according to the process of the present invention it is possible to control the sulfation degree by suitably varying the reaction temperature and/or time. For example, in the case of chitosan again, it is possible to obtain a chitosan having a sulfation degree, selective in the 6-position, higher than zero, which can arrive up to 1.

Cellulose, starch and chitin behave as chitosan.

Chondroitinsulfate and dermatansulfate behave as heparin.

In the case of guaran, it is possible to obtain depolymerized guaranes having a sulfate group on the primary hydroxy group of D-mannose.

The depolymerisation degree varies according to the molecular weight of the starting product and the stability.

In the case of cellulose and starch, depolymerized and sulfated products having a higher depolymerisation degree are obtained.

Chondroitinsulfate and dermatansulfate are less stable and the depolymerisation may go up to three- and tetrasaccharides.

Generally, the depolymerisation degree may be controlled by suitably modifying the sulfuric acid/chlorosulfonic acid ratio, the reaction time as well as the concentration of the starting product in the mixture of the two acids.

The present invention also relates, according to one of its aspects, to a chitosan 6-sulfate of formula

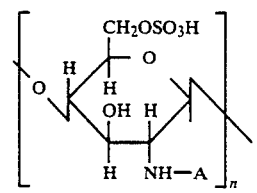

I wherein n is an integer from 4 to 6000 and A represents an hydrogen atom or, in a number of up to 30% of the subunits, an acetyl group, as well as to its salts with inorganic or organic bases or with inorganic or organic acid or its internal salts.

The expression "n is an integer from 4 to 6000" means that in the structure I above the saccharide unit may be repeated from 4 to 6000 times according to a Gaussian curve.

As the starting chitosan is prepared by deacylation of chitin, the apparent molecular mass, i.e. the value of and the percent of the acetyl groups depends on the process utilized for the preparation of said starting chitosan.

Contrary to the known chitosan sulfates in which the sulfate groups are randomly distributed both in individual glucosamine subunit and in the n units of the polysaccharide, the chitosan 6-sulfate of the present invention has a well defined structure showing only one sulfate group per glucosamine subunit.

Furthermore, contrary to the known chitosan sulfates, in which there is a disproportion between the sulfate groups and the amino groups and in which, in addition, the amino groups are generally sulfated, the 6-sulfated chitosans of the present invention show a ratio sulfate groups:amino groups which varies from 1:1 to 1:0.7, depending upon the number of acetyl groups of the starting chitosans.

Thus, the chitosane 6-sulfates are ampholytes having polyelectrolytic properties useful as sequestrants of metallic ions, dispersing agents and as condensating agents in the textile, cosmetic and food industry, as well as active ingredients in pharmaceutical compositions with biological buffering action, more particularly with antipeptic, antiacid and gastric mucous membrane protecting activity.

It is another object of the present invention, to provide a process for the preparation of chitosan 6-sulfate, more particularly represented by formula I above, characterized in that a chitosan is treated with a mixture of sulfuric acid and chlorosulfonic acid and the product thus obtained is isolated as an alkali metal salt or transformed in the acid form or in another salt.

In the mixture the two acids are concentrated; preferably their concentration is at least 95% by weight.

The ratio sulfuric acid:chlorosulfonic acid varies from 4:1 to 1:4, a ratio of about 2:1 being particularly preferred.

The reaction temperature may vary from $-20°$ to $+40°$ C.; preferably, the starting material is introduced into the mixture of the two acids at low temperature and the reaction is carried out at room temperature. After a period varying from five minutes to 2 hours, according to the reaction temperature, the reaction is completed and the chitosan 6-sulfate is isolated according to usual methods. Preferably, the reaction mixture is poured in an apolar and aprotic solvent, such as diethyl ether, in which chitosan 6-sulfate is insoluble and the product thus obtained is neutralized and purified by dialysis.

The molecular weight of the end product depends upon the reaction time and upon the water content of the reaction mixture.

The chitosan 6-sulfate thus obtained is isolated in the form of alkaline salt according to conventional techniques, for example by lyophilisation or by evaporation under reduced pressure and characterized according to known physicochemical methods.

Other salts, such as calcium salt, may be obtained starting from alkaline salts, sodium salt preferably, by exchange reaction with the appropriate salt, for example a calcium salt, by optionally utilizing an ion exchange resin.

The molecular weight of preferred starting chitosan can vary (according to the literature, for commercial preparation) from 100,000 up to 800,000, equivalent to from about 400 to about 3400 saccharide units. No end groups of such products are detectable by NMR spectroscopy.

As starting material, it may be used a chitosan previously depolymerized by a known method. The action of the sulfuric acid/chlorosulfonic acid mixture may involve a further depolymerization, beside a quantitative and selective sulfation in the 6-position.

The following examples illustrate the invention without, however, limiting it.

EXAMPLE 1

To a mixture of 20 ml of 95% sulfuric acid and 10 ml of chlorosulfonic acid, cooled to a temperature between $-4°$ and $0°$ C., there is added 1 g of heparin from pig intestinal mucosa (PROQUIFIN, lot 7926-7935, code number : D-212) having a sulfation degree of 1.95 and a molecular weight 13500, then it is stirred for 1 hour at the same temperature. After further 60 minutes at room temperature, the mixture is poured into 500 ml of cold diethyl ether ($-4°$ to $4°$ C.), the precipitate is filtered and washed with cold diethyl ether. The product thus obtained is dissolved in water, neutralized with 0.5N sodium hydroxide and dialysed against distilled water in membranes at 3500 D (THOMAS DIALYZED TUBING 3787-H47, 11 mm diameter). Thus a desalting is obtained as well as the elimination of low molecular fragments. By slow evaporation under reduced pressure, a depolymerized and supersulfated sodium heparin (code number: AH-16) is obtained in 93% yield by weight, as a powder having the following characteristics:

M.W.: $\simeq 6000$ (Formula IV, m$\simeq$9).

Elemental analysis: S: 12.93%; C: 18.48%; H: 3.30%; N: 1.76%.

Sulfation degree ($SO_3^-/COO^-$): 3.0.

IR spectrum: broad band in the region 1300–1200 $cm^{-1}$, characteristic of the sulfate groups.

Electrophoresis in hydrochloric acid: with this technique, the migration is function of the sulfation degree. FIG. 1 shows the significant increasing of the electrophoretic migration of the depolymerized and supersulfated heparin compared with the starting heparin.

Barium acetate electrophoresis: FIG. 2 shows that depolymerized and supersulfated heparin as a "slow-moving" electrophoretic characteristic, differently from the starting heparin containing both "slow-moving" and "fast moving" components.

13C-NMR spectrum: FIG. 3 shows the comparison between the spectrum of the starting heparin and that of depolymerized and supersulfated heparin. In the spectrum of the new low molecular weight heparin new signals appear, due to the effect of the depolymerisation and of the introduction of additional sulfate groups as well as to the disappearance of the 6-OH signal. The depolymerized and supersulfated heparin thus obtained shows a sulfation degree which is 53% higher than that of starting heparin without any significant decarboxylation.

EXAMPLE 2

To a mixture of 10 ml of 98% sulfuric acid and 5 ml of chlorosulfonic acid, cooled to a temperature between $-4°$ and $0°$ C., there are added 500 mg of a high molecular weight fraction (M.W. 16500, code number: D-

212/D), obtained by precipitation with ethanol and having a sulfation degree ($SO_3^-/COO^-$) of 2, of heparin PROQUIFIN, lot 7926-7935. The mixture is left to stand 1 hour at room temperature, then it is poured into 250 ml of cold diethyl ether ($-10°$ to $4°$ C.) and filtered; the precipitate thus obtained is dissolved in water, the solution is neutralized with 0.5N sodium hydroxide and dialysed against distilled water in membranes at 3500 D (THOMAS DIALYZER TUBING 3787-H47, 11 mm diameter), in order to eliminate the salts and the smallest size reaction products. By evaporation under reduced pressure, a depolymerized and supersulfated sodium heparin (code number: AH-18) is obtained in 60% yield. The product has the following characteristics:

M.W.: 3000-5000 (Formula IV, m=5-8).

Elemental analysis: S: 13.56%; C: 18.03%, H: 3.00% N: 1.70%.

Sulfatation degree ($SO_3^-/COO^-$): 2.6.

IR spectrum: broad band in the region 1300-1200 $cm^{-1}$, characteristic of the sulfate groups.

Figure 4:
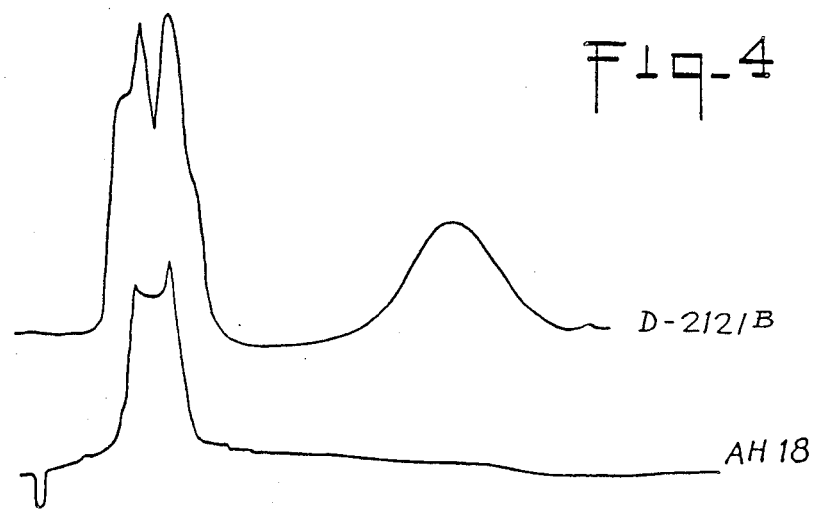

Barium acetate electrophoresis: FIG. 4 indicates that AH-18 show "slow-moving" components only, whereas the starting product also shows "fast-moving" components.

EXAMPLE 3

To a mixture of 10 ml of 98% sulfuric acid and 5 ml of chlorosulfonic acid, cooled to a temperature between $-4°$ and $0°$ C., there are added 500 mg of sodium heparin from pig intestinal mucosa (PROQUIFIN, lot 7926-7935, code number D-2212) having a sulfation degree ($SO_3^-/COO^-$) of 1.95.

The mixture is left to stand 1 hour at room temperature, then it is poured into 250 ml of cold diethyl ether ($-10°$ to $4°$ C.), and afterwards treated as described in Examples 1 and 2. Thus, a depolymerized and supersulfated sodium heparin (code number: AH-19) is obtained in 90% yield. The product has the following characteristics:

M.W.: $\approx 6000$ (Formula IV, m=9.

Sulfation degree ($SO_3^-/COO^-$): 3.0.

IR spectrum: broad band in the region 1300-1200 $cm^{-1}$, characteristic of the sulfate groups.

Figure 5:
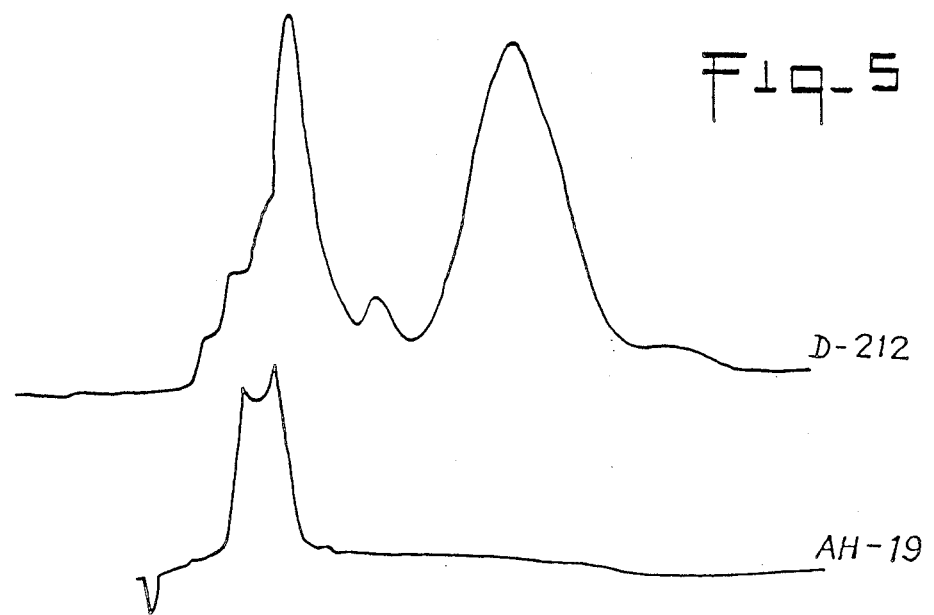

Barium acetate electrophoresis: FIG. 5 indicates that AH-19 shows "slow-moving" components only, whereas the starting product also shows "fast moving" components.

EXAMPLE 4

To a mixture of 10 ml of 98% sulfuric acid and 5 ml of 95% chlorosulfonic acid, cooled to a temperature between $-4°$ and $0°$ C., there are added 500 mg of a mean molecular weight heparin fraction (M.W.: $\approx 10000$, code number: D-212/2), obtained by fractionation with ethanol of heparin PROQUIFIN, lot 7926-7935, said fraction having a sulfation degree ($SO_3^-/COO^-$) of 1.5 and a barium acetate electrophoretic pattern which shows a very important "fast moving" component. The mixture is left to stand 1 hour under stirring at room temperature, then it is poured into 250 ml of cold diethyl ether ($-10°$ to $4°$ C.), and afterwards treated as described in Examples 1 and 2. Thus, a depolymerized and supersulfated sodium heparin (code number: AH-17) is obtained having the following characteristics:

M W.: 3000-5000 (Formula IV, m=5-8.

Elemental analysis: S: 12.70%; C: 17.24%; H: 3.10%; N: 1.67%.

Sulfation degree ($SO_3^-/COO^-$): 2.5.

IR spectrum: broad band in the region 1300-1200 $cm^{-1}$, characteristic of the sulfate groups.

Figure 6:
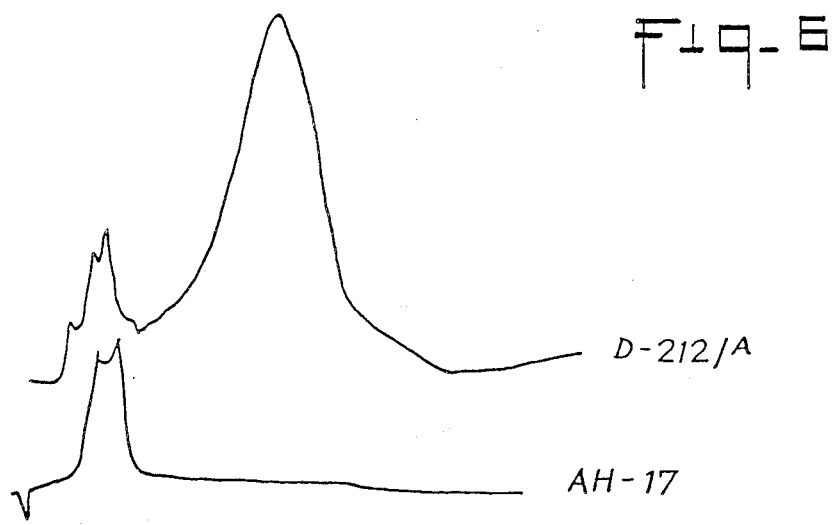

Barium acetate electrophoresis: FIG. 6 indicates that AH-17, compared to the starting heparin fraction, shows a "slow-moving" component only.

EXAMPLE 5

To a mixture of 20 ml of 95% sulfuric acid and 10 ml of 98% chlorosulfonic acid, cooled to a temperature between $-4°$ and $0°$ C., there is added 1 g of heparin from pig intestinal mucosa (PROQUIFIN, lot 7926-7935, code number: D-212) having a sulfation degree of 1.95, then the reaction mixture is stirred 1 hour at room temperature. The mixture is poured into 500 ml of cold diethyl ether ($-4°$ to $4°$ C.), the precipitate is filtered and washed with cold diethyl ether. The product thus obtained is dissolved in 0.1M calcium chloride aqueous solution, then 0.5M calcium hydroxide is added thereto up to pH 8. The solution is dialysed against 500 ml of 0.1M calcium chloride solution and then against distilled water. By slow evaporation under reduced pressure, a calcium salt of a depolymerized and supersulfated heparin is obtained as a white powder.

EXAMPLES 6 to 10

To a mixture of 10 ml of 98% sulfuric acid and 5 ml of chlorosulfonic acid, cooled to a temperature between $-4°$ and $0°$ C., there are added 500 mg of heparin from pig intestinal mucosa (PROQUIFIN, lot 7926-7935, code number: D-212) having a sulfation degree of 1.95 and a molecular weight 13500. By operating as described in Example 1, a depolymerized and supersulfated heparin (code number: AH-104) is obtained, in 98% yield.

The same procedure and conditions are followed in 4 parallel experiments in which the same starting heparin is used. There are obtained the products designated by their code numbers AH-103, AH-105, AH-106 and AH-107. The characteristics of the products thus obtained as well as those of the product coded AH-104 are given in Table IV.

TABLE IV

| Ex. | Product | Elemental Analysis | | | | Sulfation degree | Yield by weight |
|---|---|---|---|---|---|---|---|
| | | S % | C % | H % | N % | | |
| 6 | AH-104 | 14.54 | 15.42 | 2.84 | 1.43 | 2.9 ± 0.1 | 98% |
| 7 | AH-103 | 14.63 | 15.53 | 2.76 | 1.43 | 2.8 ± 0.1 | 89% |
| 8 | AH-105 | 14.48 | 15.43 | 2.61 | 1.44 | 3.0 ± 0.1 | 67% |
| 9 | AH-106 | 14.54 | 15.53 | 2.81 | 1.46 | 2.8 ± 0.1 | 96% |
| 10 | AH-107 | 14.12 | 15.65 | 2.80 | 1.40 | 3.0 ± 0.1 | 77% |

Molecular weight: $\approx 6000$ for the 5 products
IR spectrum: the 5 products show a spectrum identical to that of compound AH-16 described in Example 1.
Electrophoresis in hydrochloric acid: the electrophoretic profiles are indentical to those of FIG. 1 for both the starting heparin and the 5 products
Barium acetate electrophoresis: the electrophoretic profiles are identical to those of FIG. 2 for both the starting heparin and the 5 products, apart from the fact that the traces relative to the 5 products do not show the background noise - caused by a temporary defect of the tracing pen or of the paper - observed in the horizontal cart of the graph of FIG. 2 relative to AH-16
13C-NMR spectrum: the 5 products and the starting compound present the same spectra as those given in FIG. 3.

The 5 compounds thus obtained are identical each other and identical to the compound described in Example 1 as well.

EXAMPLES 11 to 14

In 4 parallel experiments, to a mixture of 10 ml of 98% sulfuric acid and 5 ml of chlorosulfonic acid, cooled to −4°–0° C., there are added 500 mg of previously lyophilized heparin from pig intestinal mucosa (DIOSYNTH batch CH/N 655, code number: D-479), having a sulfation degree ($SO_3^-/COO^-$) of 2.1 and a molecular weight of about 11000. The reaction mixture is left to stand 1 hour at 0° C., then it is poured into 250 ml of diethyl ether previously cooled (between −10° C. and +4° C.) By operating as described in Example 1 the products of Table V are obtained.

TABLE V

| Ex. | Product | Elemental Analysis | | | | Sulfation degree | Yield by weight |
|---|---|---|---|---|---|---|---|
| | | S % | C % | H % | N % | | |
| 11 | AH-108 | 14.88 | 15.29 | 2.52 | 1.47 | 3.1 ± 0.1 | 90% |
| 12 | AH-109 | 14.43 | 15.48 | 2.72 | 1.44 | 3.0 ± 0.1 | 106% |
| 13 | AH-110 | 14.45 | 15.72 | 2.76 | 1.50 | 2.9 ± 0.1 | 65% |
| 14 | AH-111 | 14.55 | 15.08 | 2.60 | 1.41 | 3.0 ± 0.1 | 23% |

Molecular weight: ≃6000 for the 4 products.

IR spectrum: broad band between 1300 and 1200 $cm^{-1}$, characteristic of the sulfate group.

Electrophoresis in hydrochloric acid: FIG. 6 shows the traces of the starting heparin D-479 and of one of the 4 samples obtained in the different experiments (AH-108). The traces of the other three compounds are identical. This figure evidences the significant increase of the electrophoretic migration of the depolymerized and supersulfated heparin in comparison with the starting heparin.

Figure 7:
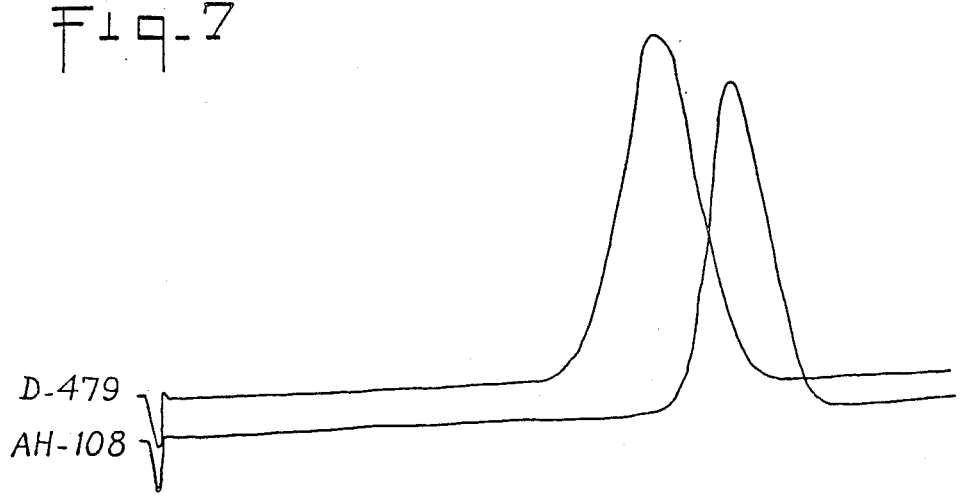

Barium acetate electrophoresis: FIG. 7 shows the traces of the starting heparin D-479 and of AH-108. It results that the depolymerized and supersulfated heparin has a "slow-moving" electrophoretic profile, unlike the starting heparin containing "slow-moving" components as well as "fast-moving" components. The traces of the products AH-109, AH-110 and AH-111 are identical to that of AH-108.

EXAMPLE 15

To a mixture of 10 ml of 98% sulfuric acid and 5 ml of chlorosulfonic acid, cooled to a temperature between −4° and 0° C., there are added 500 mg of heparin from pig intestinal mucosa (THERORMON, batch 575/018, code number: D-98) having a sulfatation degree of 1.8 and a molecular weight 135.00. By operating as described in Example 1, a depolymerized and supersulfated heparin is obtained, in 75% yield. The product has the following characteristics:

M.W.: ≃6000.

Elemental analysis: S: 13.90%; C: 15.75%; H: 2.96%; N: 1.48%.

Sulfatation degree ($SO_3^-/COO^-$): 2.8±0.1.

IR spectrum: broad band in the region 1300–1200 $cm^{-1}$, characteristic of the sulfate groups.

Figure 8:
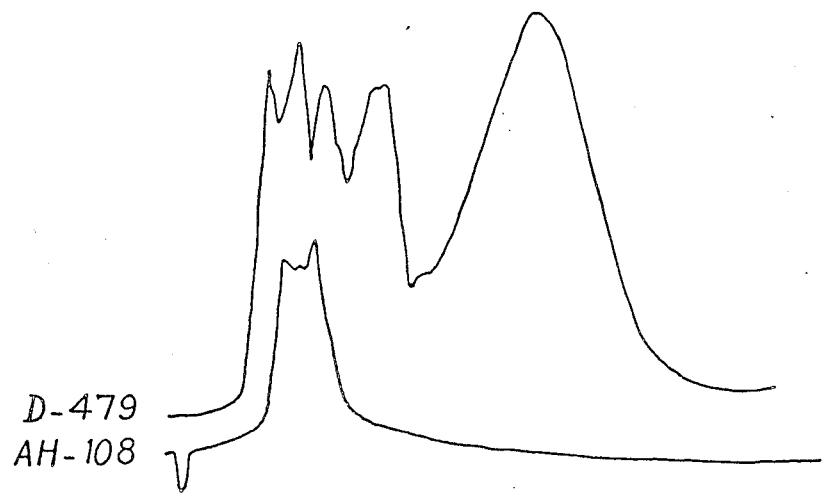

Electrophoresis in hydrochloric acid: FIG. 8 shows the traces of the starting heparin D-98 and of the product AH-118. A significant increasing of the electrophoretic migration of AH-118 compared with the starting heparin D-98, may be observed. FIG. 8 shows also that the compound AH-118 possesses a photodensitometric outline analogous to those of compounds AH-16 (Example 1, FIG. 1) and AH-17 (Example 4, FIG. 6) whereas the starting heparin D-98 appears very heterogeneous and completely different from the starting heparins utilized in Examples 1 and 4.

Figure 9:
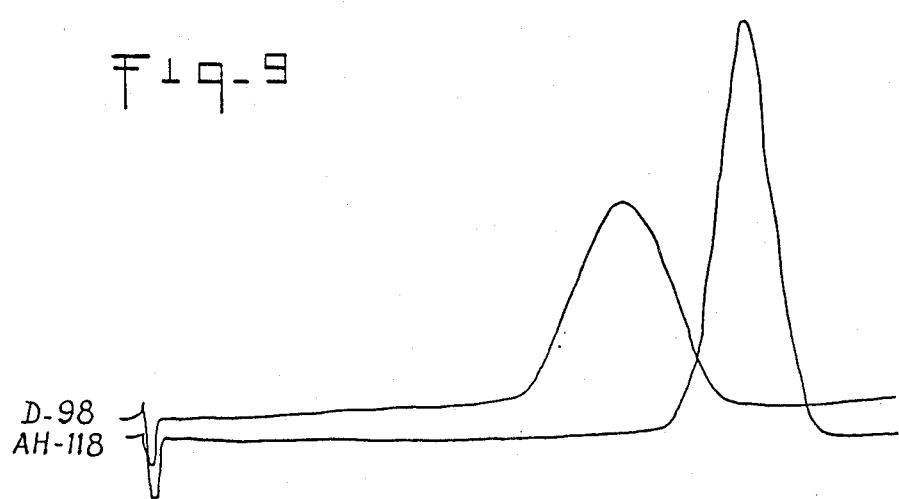
Figure 10:
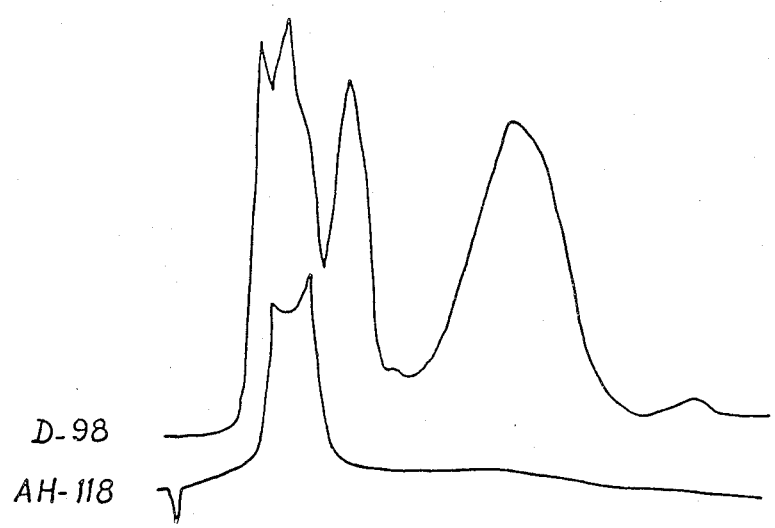

Barium acetate electrophoresis: FIG. 10 indicates that AH-118 shows a "slow-moving" electrophoretic characteristic which is different from that of the starting heparin D-98 showing both "slow-moving" and "fast-moving" components. FIG. 10 also confirms that data of FIG. 9 and moreover surprisingly shows that compound AH-118 is not significantly different from AH-108 of Example 11, though the starting heparins are quite different.

EXAMPLE 16

To a mixture of 20 ml of 95% sulfuric acid and 10 ml of chlorosulfonic acid, previously cooled to 0°–4° C., there are added 500 mg of chitosan ANIC, lot 116 containing 15–20% of N-acetyl groups. The mixture is stirred at the same temperature for about 1 hour, then it is poured into previously cooled diethyl ether. The precipitate which forms is filtered and neutralized with a potassium bicarbonate solution. After a dialysis in THOMAS DIALYZER TUBINC at 8500 D, a chitosan 6-sulfate (P 211 - SR 95338) is obtained, having the following characteristics:

M.W.: about 10,000.

Substitution degree (conductimetric method): 1.

IR spectrum: broad band in the region 1300–1200 $cm^{-1}$, characteristic of the sulfate groups.

Figure 11:
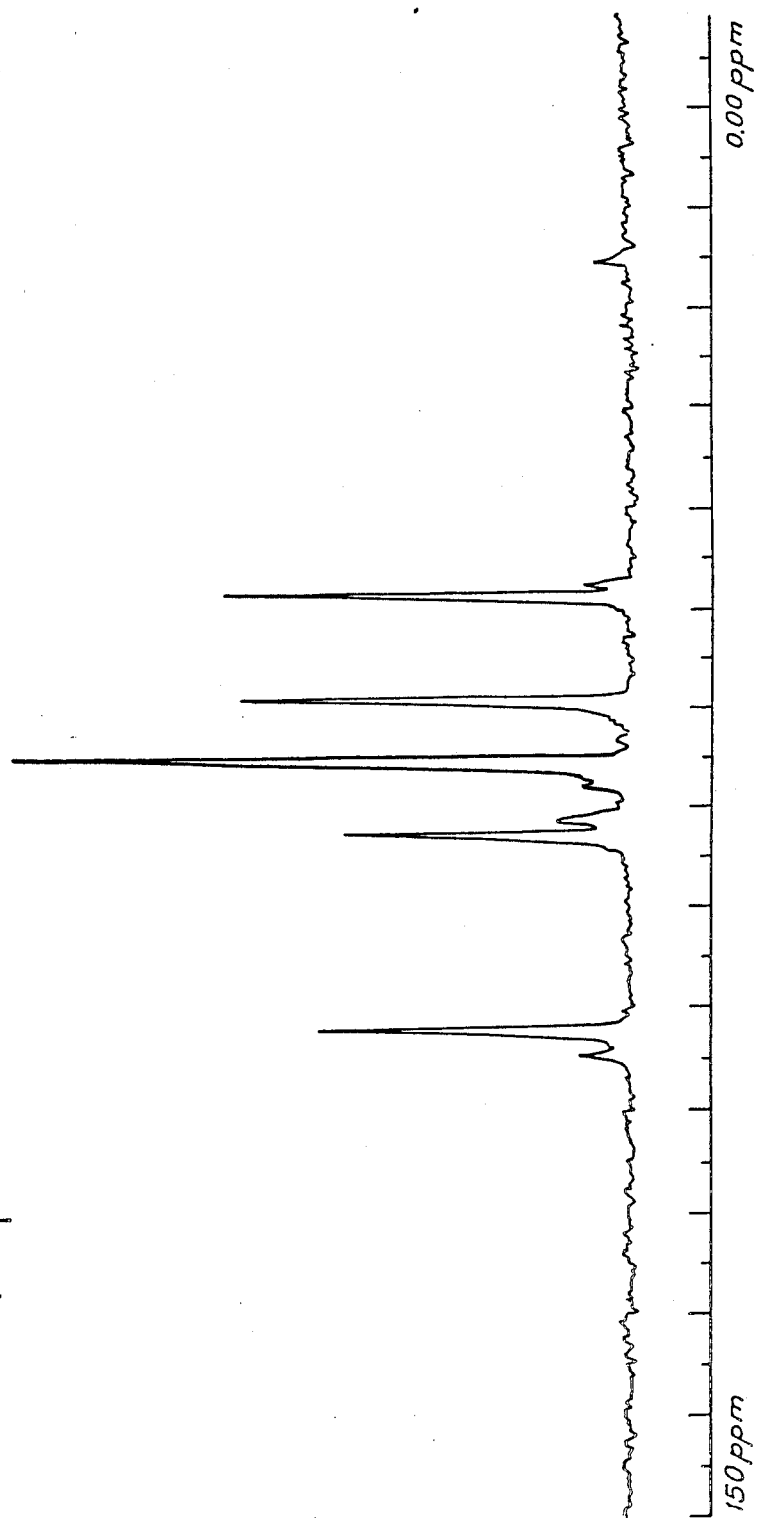

13C-NMR spectrum: FIG. 11 shows the complete disappearance of the signal of the primary hydroxy groups and the appearance of the signal relating to the 6-O sulfate groups. No N-sulfate or 3-O-sulfate signal is present.

EXAMPLE 17

To a mixture of 20 ml of 95% sulfuric acid and 10 ml of 98% chlorosulfonic acid, cooled to a temperature between −4° and 0° C., there is added 1 g of chitosan ANIC, lot 116. The reaction mixture is left to stand 30 minutes at room temperature, then it is poured into 500 ml of previously cooled diethyl ether. After filtration, the precipitate is washed in water and neutralized with a solution of 0.5N sodium hydroxide, then it is dialyzed against distilled water in membranes at 8000D (THOMAS DIALYZER TUBING) and evaporated under reduced pressure. Thus, a chitosan 6-sulfate is obtained in 90% yield. The product has the following characteristics:

Substitution degree (conductimetric method): 0.5, namely, 50% only of the hydroxy group in 6 position has been sulfated.

IR spectrum: broad band in the region 1300–1200 $cm^{-1}$, characteristic of the sulfate groups.

13C-NMR spectrum: diminution of the signal relating to the primary hydroxy group and apparatus of the signal relating to the sulfate group.

EXAMPLE 18

(a) To a solution of 1 g of chitosan ANIC, lot 116, in 50 ml of 30% acetic acid, there are added 2.3 ml of 0.5M nitrous acid, prepared from 10 ml of 0.5M barium nitrite monohydrate and 10 ml of 0.5M sulfuric acid. The mixture is stirred 12 hours at room temperature, concentrated under reduced pressure and treated with acetone. The precipitate which forms is filtered, washed with acetone, dried, dissolved in water and treated with 30 mg of sodium borohydride. After 12 hours at room temperature, the excess of sodium borohydride is destroyed with "AMBERLITE IP 120 H+" and the boric acid is eliminated by evaporation under reduced pressure in the presence of methanol. Thus a depolymerized chitosan is obtained, having a molecular weight much lower (about 2500) than that of the starting chitosan.

(b) To a mixture of 20 ml of 95% sulfuric acid and 10 ml of 98% chlorosulfonic acid, cooled to a temperature between −4° and 0° C., there is added 1 g of the above depolymerized chitosan. The reaction mixture is left to stand 1 hour at room temperature, then it is poured into 250 ml of previously cooled diethyl ether; the precipitate which forms is filtered and washed with cold diethyl ether. The product is dissolved in water and neutralized with a 0.5M sodium hydroxide solution. After desalting by chromatography on "Sephadex G25", a depolymerized chitosan 6-sulfate is obtained in a 90% yield. The product has the following characteristics:
M.W.: 2000.
Substitution degree: 1.
IR spectrum: broad band in the region 1300–1200 $cm^{-1}$, characteristic of the sulfate groups.
13C-NMR spectrum: disappearance of the signal of the primary hydroxy groups and appearance of a new signal due to the sulfate groups.

EXAMPLE 19

To a mixture of 20 ml of 95% sulfuric acid and 10 ml of 98% chlorosulfonic acid, cooled to 0°–4° C., there is added 1 g of cellulose microcristalline (M.W. 20000). The reaction mixture is left 1 hour under stirring, then additional 30 ml of the mixture sulfuric acid:chlorosulfonic acid 2:1 are added thereto. After 30 minutes, the mixture is poured into 500 ml of cold diethyl ether, then it is filtered, the precipitate is washed with diethyl ether and dissolved in water. By neutralization with a 0.5M sodium hydroxide solution, dialysis in membranes at 3500 D (THOMAS DIALYZER TUBING 3787-H 47, 11 mm diameter) and evaporation under pressure, a cellulose 6-sulfate is obtained, with a 36% yield of dialysable fraction and 29% yield of non-dialysable fraction. The product has the following characteristics:
Substitution degree (conductimetric method): 1.
IR spectrum: broad band in the region 1300–1200 $cm^{-1}$, characteristic of the sulfate groups.
Molecular weight: 3400.

EXAMPLES 20 to 22

In three parallel experiments, 500 mg of heparin from pig intestinal mucosa (DIOSYNTH, batch CH/N 665, code n. D-479) having a sulfation degree ($SO_3^-$/$COO^-$) 2.1 and a molecular weight 11000 are added to 15 ml of a mixture of 98% sulfuric acid and 98% chlorosulfonic acid in the following ratios:
Example 20: 1:4
Example 21: 1:1
Example 22: 4:1
By operating as described in Example 1, three depolymerized and supersulfated heparins, having the characteristics given in Table VI, are obtained.

TABLE VI

| Example (code NO) | Sulfation degree | Molecular weight | Yield % by weight |
|---|---|---|---|
| 20 (AH-67) | 2.5 | 4000 | 89.9 |
| 21 (AH-65) | 2.5 | 3800 | 86.8 |
| 22 (AH-68) | 2.8 | 4500 | 77.4 |

EXAMPLE 23

To a mixture of 10 ml of 98% sulfuric acid and 5 ml of 98% chlorosulfonic acid, at the temperature of 0°–4° C., 1 g of guaran (AGOGUM F-90, lot 433) is added. After 1 hour at the same temperature, by operating as described in Example 1, a guaran 6-sulfate is isolated as sodium salt (code No. AH-102). The product has the following characteristics:
Substitution degree (conductimetric method): 1.
IR spectrum: broad band in the region between 1300 and 1200 $cm^{-1}$, characteristic of the sulfate group
Yield: 26% by weight

EXAMPLE 24

To a mixture of 20 ml of 95% sulfuric acid and 10 ml of 98% chlorosulfonic acid, cooled to 0°–4° C., g of chitin (SIGMA, lot 12 F-7060) is added. The reaction mixture is left to stand 1 hour at the same temperature. Then, by operating as described in Example 1, after dialysis and evaporation under reduced pressure a chitin 6-sulfate is obtained and isolated as sodium salt (code N° AH-50). The product has the following characteristics:
Substitution degree (conductimetric method): 1.
IR spectrum: broad band in the region between 1300 and 1200 $cm^{-1}$, characteristic of the sulfate group
13C-NMR spectrum disappearance of the signal of the primary hydroxy group and appearance of the signal of sulfate groups.
Yield: 70% by weight

EXAMPLE 25

To a mixture of 15 ml of 95% sulfuric acid 98% chlorosulfonic acid 2:1, cooled to 0°–4° C., there are added 500 mg of chonroitinsulfate TAKEDA (lot BB-185, No. Code: D-267) having a molecular weight 22000 and containing 18% of moisture After 1 hour at room temperature, the mixture is poured into 500 ml of cold diethyl ether. The precipitate which forms is dissolved in water, the solution is neutralised with 0.5M sodium hydroxide, then it is dialysed in tubes at 3500 D (THOMAS DIALYZER TUBING, diameter 15 mm). By evaporating under reduced pressure a depolymerized and supersulfated chondroitinsulfate (code No. AH 69) having the following characteristics is obtained:
IR spectrum: broad band in the region 1300–1200 $cm^{-1}$, characteristic of the sulfate groups.
Molecular weight: 2000.

EXAMPLE 26

To a mixture of 10 ml of 98% sulfuric acid and 5 ml of 98% chlorosulfonic acid, there is added 500 ml of dermatansulfate OPOCRIN (lot 7-8 HF) having a molecular weight 27000 and a substitution degree ($SO_3^-$/$COO^-$): 1. By operating as described in Example 25, a depolymerized and supersulfated dermatansulfate (code N°. AH-79) is obtained. The product has the following characteristics:
Substitution degree ($SO_3^-$/$COO^-$), conductimetric method ): 2.8.
IR spectrum broad band in the region between 1300 and 1200 $cm^{-1}$, characteristic of sulfate groups.
Molecular weight 2000.

What we claim is:
1. A process for the depolymerisation and sulfation of polysaccharides, which comprises reacting the polysaccharides selected from the group consisting of heparansulfates, chitosan, chitin, cellulose, starch, guaran, the chondroitinsulfates, inulin, dermatansulfate, keratan, the mannans, scleroglucan, the galactomannans, the dextrans, the galactans, xanthan and, with a mixture consisting only of sulfuric acid and chlorosulfonic acid.

2. A process for the depolymerisation and sulfation of polysaccharides, which comprises reacting said polysaccharides selected from the group consisting of chitosan, chitin, microcrystalline cellulose, guaran, the chondroitinsulfates, and dermatansulfate, with a mixture consistent only of sulfuric acid and chlorosulfonic acid.

3. A process as claimed in one of claims 1 and 2 in which the reaction is carried out at temperature of from $-20°$ to $+40°$ C.

4. A process as claimed in any one of claims 1 or 2 in which the concentration of the two acids is at least 95% by weight.

5. A process as claimed in one of claims 1 or 2 in which the ratio sulfuric acid:chlorosulfonic acid is from 4:1 to 1:1.

6. A process as claimed in one of claims 1 or 2 in which the ratio sulfuric acid:chlorosulfonic acid is about 2:1.

7. A process as claimed in one of claims 1 or 2 in which the depolymerized and sulfated polysaccharide is isolated as sodium salt.

8. A process as claimed in one of claims 1 or 2 in which the depolymerized and sulfated polymerized and sulfated polysaccharide is transformed into one of its salts.

9. A process as claimed in claim 7 in which the sodium salt is transformed into another salt of the depolymerized and sulfated polysaccharide by exchange with the appropriate salt.

10. A process as claimed in one of claims 1 or 2 in which the starting polysaccharide is previously depolymerized.

11. A chitosan 6-sulfate of formula

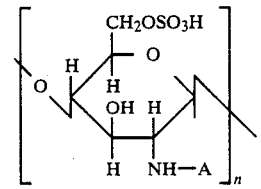

wherein n is an integer from 4 to 6000 and A represents an hydrogen atom or, in a number of up to 30% of the n subunits, an acetyl group; or a salt thereof with an inorganic or organic acid or with an inorganic or organic base or an internal salt thereof.

12. A process as claimed in claim 1 wherein the polysaccharide is a chitosan and said chitosan is added, at $0°-4°$ C., to a mixture of sulfuric acid and cholorosulfonic acid and, after a period of from five minutes to two hours at room temperature, the chitosan 6-sulfate product is isolated as an alkali metal salt or converted into the acid form or another salt.

13. A process as claimed in claim 12, in which the concentration of the two acids in the mixture is at least 95% by weight.

14. A process as claimed in one of claims 12 and 13, in which the ratio sulfuric acid:chlorosulfonic acid is about 2:1.

15. A process as claimed in one of claims 12, 13, or 14 in which the starting chitosan is previously depolymerized.

* * * * *